US008093397B2

(12) United States Patent
Sinha et al.

(10) Patent No.: US 8,093,397 B2
(45) Date of Patent: *Jan. 10, 2012

(54) ACTIVATORS FOR OLIGONUCLEOTIDE SYNTHESIS

(75) Inventors: Nanda Sinha, Boxboro, MA (US); William Edward Zedalis, Fitchburg, MA (US); Gregory Keith Miranda, Princeton, MA (US)

(73) Assignee: Avecia Biotechnology, Inc., Milford, MA (US)

( * ) Notice: Subject to any disclaimer, the term of this patent is extended or adjusted under 35 U.S.C. 154(b) by 339 days.

This patent is subject to a terminal disclaimer.

(21) Appl. No.: 12/287,116

(22) Filed: Oct. 6, 2008

(65) Prior Publication Data

US 2009/0085006 A1  Apr. 2, 2009

Related U.S. Application Data

(63) Continuation of application No. 10/482,441, filed as application No. PCT/GB02/03029 on Jul. 1, 2002, now Pat. No. 7,501,505.

(60) Provisional application No. 60/302,717, filed on Jul. 3, 2001.

(51) Int. Cl.
*C07D 275/06* (2006.01)

(52) U.S. Cl. ........................................ 548/211; 548/210

(58) Field of Classification Search ........................ None
See application file for complete search history.

(56) References Cited

U.S. PATENT DOCUMENTS

| 757,650 | A | 4/1904 | Chausse |
| 3,325,475 | A | 6/1967 | Vacek |
| 4,683,233 | A | 7/1987 | Salzburg et al. |
| 5,034,534 | A | 7/1991 | Milstein |
| 5,639,875 | A | 6/1997 | Bhongle |
| 6,096,881 | A | 8/2000 | Han et al. |
| 6,274,725 | B1 | 8/2001 | Sanghvi et al. |
| 7,247,720 | B2 * | 7/2007 | Sinha .......................... 536/25.33 |
| 7,501,505 | B2 * | 3/2009 | Sinha et al. ................. 536/25.34 |
| 7,635,772 | B2 * | 12/2009 | McCormac ................. 536/25.31 |
| 2006/0041114 | A1 | 2/2006 | Sinha et al. |

FOREIGN PATENT DOCUMENTS

| EP | 0 061 434 A1 | 3/1982 |
| EP | 0 274 023 A1 | 11/1987 |
| WO | WO 98/16450 | 4/1998 |
| WO | WO 99/62922 | 12/1999 |
| WO | WO/03/004512 | 1/2003 |

OTHER PUBLICATIONS

Kawada, S., et al. "Agrochemical Germicides Containing Saccharin Derivatives," *Chemical Abstracts Service*, Database Accession No. 79:74918 (1973).
Villalgordo, J.M., et al., "Reactions of 2-Monosubstituted 3-Amino-2H-Azirines with NH-Acidid Heterocyles," *Helvetica Chimca ACTA*, 75:2270-2282 (1992).
Abramovitch, R.A., et al. "New Ring System from 1,2-Benzisothiazole-1,1-Dioxides and Related Compounds," *Tetrahedron*, 52:3339-3354 (1996).

Moriguchi, T., et al., "Synthesis and Properties of Aminocylamido-AMP: Chemical Optimization for the Construction of an N-Acyl Phosphoramidate Linkage," *J. Org. Chem.*, 65:8229-8238 (2000).
Berner, S., et al., "Studies on the role of tetrazole in the activation of phosphoramidites", *Nucleic Acids Research*, 1989, 17(3) : 853-864.
Dahl, B.H., et al., "Mechanistic studies on the phosphoramidite coupling reaction in oligonucleotide synthesis. I. Evidence for nucleophilic catalysis by tetrazole and rate variations with the phosphorus substituents", *Nucleic Acids Research* , 1987, 15(4) : 1729-1743.
Drutsa, V.L. et al., "Investigation of activation of phosphate groups in mono- and oligonucleotides with mestitoyl choloride", *Nucleic Acids Research*, 1978, 5(1) : 185-193.
Eadie, S. et al., "Guanine modification during chemical DNA synthesis", *Nucleic Acids Research*, 1987, 15 (20) : 8333-8349.
Efimov, V.A., et al., "Application of new catalytic phosphate protecting groups for the highly efficient phosphotriester oligonucleotide synthesis", *Nucleic Acids Research*, 1986, 14 (16) : 6525-6540.
Efimov, V.A., et al., "Improved rapid phosphotriester synthesis of oligodeoxyribonucleotides using oxygen-nucleophilic catalysts", *Nucleic Acids Research*, 1985, 13 (10) : 3651-3666.
Hotoda, H., et al., "Pre-activation strategy for oligodeoxyribonucleotide synthesis using triaryloxydichlorophosphoranes in the phosphotriester method", *Nucleic Acids Research*, 1989, 17 (13) : 5291-5305.
Pless, R.D., et al., "Solid support synthesis of oligothymidylates using phosphorochloridates and 1-alkylimidazoles", *Nucleic Acids Research* , 1975, 2 (6) : 773-786.
Seth, A.K., et al., "A study of the efficiency and the problem of sulfonation of several condensing reagents and their mechanisms for the chemical synthesis of deoxyoligoribonucleotides", *Nucleic Acids Research*, 1980, 8 (22), 5445-5459.

(Continued)

*Primary Examiner* — Eric S Olson
(74) *Attorney, Agent, or Firm* — Timothy E. Tinkler

(57) ABSTRACT

A process for the synthesis of oligonucleotides using phosphoramidite chemistry is provided. The process employs as activator a 1,1-dioxo-1,2-dihydro-1λ$^6$-benzo[d]isothiazol-3-one, preferably in the presence of an organic base. The 1,1-dioxo-1,2-dihydro-1λ$^6$-benzo[d]isothiazol-3-one is represented by the following structural formula:

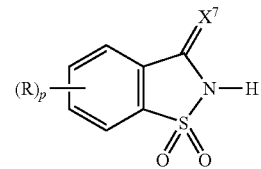

wherein p is 0 or an integer from 1 to 4; X7 is O or S; R for each occurrence is a substituent, preferably each independently, a halo, a substituted or unsubstituted aliphatic group, —NR11R12, —OR13, —OC(O)R13, —C(O) OR13, or cyano; or two adjacent R groups taken together with the carbon atoms to which they are attached form a six membered saturated or unsaturated ring; R11 and R12 are each, independently, —H, a substituted or unsubstituted aliphatic group, a substituted or unsubstituted aryl group, or a substituted or unsubstituted aralkyl group; and R13 is a substituted or unsubstituted aliphatic group, a substituted or unsubstituted aryl group, or a substituted or unsubstituted aralkyl group. Preferred organic bases are pyridine, 3-methylpyridine, or N-methylimidazole.

3 Claims, No Drawings

OTHER PUBLICATIONS

Sproat, B.S., et al., "Highly efficient chemical synthesis of 2'-O-methyloligoribonucleotides and tetrabiotinylated derivatives; novel probes that are resistant to degradation by RNA or DNA specific nucleases", *Nucleic Acids Research*, 1989, 17 (9), 3373-3386.

Vargeese, C., et al., "Efficient activation of nucleoside phosphoramidites with 4,5-dicyanoimidazole during oligonucleotide synthesis", *Nucleic Acids Research*, 1998, 26 (4), 1046-1050.

Wincott, F., et al., "Synthesis, deprotection, analysis and purification of RNA and ribozymes", *Nucleic Acids Research*, 1995, 23 (14) : 2677-2684.

de Vroom, E., et al., "Use of a 1-hydroxybenzotriazole activated phosphorylating reagent towards the synthesis of short RNA fragments in solution", *Nucleic Acids Research*, 1986, 14 (14) : 5885-5900.

Zarytova, V.F., et al., "General scheme of the phosphotriester condensation in the oligodeoxyribonucleotide synthesis with arylsulfonyl chlorides and arylsulfonyl azolides", *Nucleic Acids Research*, 1984, 12 (4) : 2091-2110.

Hayakawa, Y., et al., "Benzimidazolium Triflate as an Efficient Promoter for Nucleotide Synthesis via the Posphoramidite Method", *J. Org. Chem.*, 1996, 61 (23), 7996-7997.

Fourrey, J.L., et al., "A New Method for the Synthesis of Branched Ribonucleotides", *Tetrahedron Letters*, 1987, 28 (16), 1769-1772.

Pon, R.T., "Enhanced Coupling Efficiency Using 4-Dimethylaminopyridine (DMAP) and Either Tetrazole, 5-(o-Nitrophenyl)Tetrazole, or 5-(p-Nitrophenyl) Tetrazole in the Solid Phase Synthesis of Oligoribonucleotides by the Phosphoramidite Procedure", *Tetrahedron Letters*, 1987, 28 (32), 3643-3646.

* cited by examiner

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence

```
<220> FEATURE:
<223> OTHER INFORMATION: short DNA sequence synthesized by modified
      phosphoramadite chemistry

<400> SEQUENCE: 1
tctcccagcg tgcgccat                                                 18
```

ACTIVATORS FOR OLIGONUCLEOTIDE SYNTHESIS

RELATED APPLICATIONS

This application is a continuation of U.S. application Ser. No. 10/482,441, filed Aug. 13, 2004, which is the U.S. National Stage of International Application No. PCT/GB02/03029, filed on Jul. 1, 2002, published in English, which claims the benefit of U.S. Provisional Application No. 60/302,717, filed on Jul. 3, 2001. The entire teachings of the above applications are incorporated herein by reference.

BACKGROUND OF THE INVENTION

Synthetic oligonucleotides are important diagnostic tools for the detection of genetic and viral diseases. In addition, oligonucleotides and modified oligonucleotides are of interest as therapeutic candidates that inhibit gene expression or protein function. Large scale synthesis of oligonucleotides for use as therapeutic candidates has become increasingly important since FDA approval of an oligonucleotide analog for the treatment of cytomegalovirus (CMV), and several other oligonucleotide analogs are currently in clinical trials. Kilogram quantities of a purified oligonucleotide analog are needed for each clinical trial.

Preparation of an oligonucleotide using phosphoramidite methodology involves condensation of a nucleoside phosphoramidite and a nucleoside or a nascent oligonucleotide. The condensation reaction (also referred to herein as the coupling reaction) requires an activator (alternatively known as a coupling agent) which facilitates the reaction. The most commonly used activator is the nucleophilic activator 1H-tetrazole. However, 1H-tetrazole is explosive and, therefore, can be hazardous to use in large scale syntheses.

1H-tetrazole is a weak acid which protonates the trivalent phosphorus of the phosphoramidite during the first step of activation. A tetrazolide anion then displaces the dialkylamine group (e.g., N,N-diisopropyl amine) of the phosphoramidite during a second slower step to form a tetrazolyl intermediate which then reacts rapidly with the 5'-primary alcohol group of a nucleoside or a nascent oligonucleotide. When sterically hindered phosphoramidites, such as t-butyldimethylsilyl protected ribonucleoside phosphoramidites or 2'-O-methylnucleoside phosphoramidites, are used for oligonucleotide synthesis alternative activators are often needed to increase the rate of the coupling reaction. Alternative activators, such as 5-ethylthio-1H-tetrazole, 5-(p-nitrophenyl)-1H-tetrazole, and benzimidazolium triflate, are often more acidic than tetrazole and, thus, accelerate the rate of protonation of the trivalent phosphorous thereby increasing the rate of condensation.

However, since tetrazole, 5-ethylthio-1H-tetrazole, 5-(p-nitrophenyl)-1H-tetrazole, and benzimidazolium triflate are acidic, they can cause premature deprotection of the 5'-hydroxy protecting group of a phosphoramidite monomer which is typically an acid labile group. Premature deprotection can produce oligonucleotide impurities that are one base longer than the desired product (referred to herein as "N+1 impurities") and are difficult to separate from the desired product. The longer coupling times generally necessary for RNA synthesis and large scale synthesis result in an increase in premature deprotection of phosphoramidites.

Therefore, non-explosive activators that promote condensation of a nucleoside phosphoramidite with a nucleoside or a nascent oligonucleotide and which may be employed without increasing side products are needed in order to make oligonucleotides more readily available for diagnostic and therapeutic use.

SUMMARY OF THE INVENTION

It has been discovered that a 1,1-dioxo-1,2-dihydro-1λ6-benzo[d]isothiazol-3-one will promote condensation of a nucleoside phosphoramidite and nucleoside monomer or a nascent oligonucleotide. The 1,1-dioxo-1,2-dihydro-1λ6-benzo[d]isothiazol-3-one can be represented by Structural Formula I:

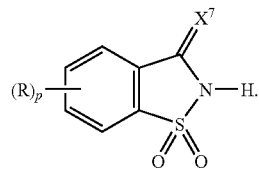

In Structural Formula I, p is 0 or an integer from 1 to 4. R for each occurrence is a substituent, preferably each independently, a halo, a substituted or unsubstituted aliphatic group, —NR11R12, —OR13, —OC(O)R13, —C(O)OR13, cyano, a substituted or unsubstituted aryl, a substituted or unsubstituted heterocyclyl, —CHO, —COR13, —NHCOR13, a substituted or unsubstituted aralkyl, halogenated alkyl (e.g., trifluoromethyl and trichloromethyl), or —SR13. Preferably, R is halo, a substituted or unsubstituted aliphatic group, —NR11R12, —OR13, —OC(O)R13, —C(O)OR13, or cyano. Alternatively, two adjacent R groups taken together with the carbon atoms to which they are attached form a six membered saturated or unsaturated ring. Preferably, the six membered ring formed is an aromatic ring. R11 and R12 are each, independently, —H, a substituted or unsubstituted aliphatic group, a substituted or unsubstituted aryl group, a substituted or unsubstituted aralkyl group; or together with the nitrogen to which they are attached form a heterocyclyl group. R13 is a substituted or unsubstituted aliphatic group, a substituted or unsubstituted aryl group, or a substituted or unsubstituted aralkyl group. X7 is O or S. Preferably, X7 is O. It is particularly preferred that X7 is O and p is 0.

In a preferred embodiment, a salt complex of the 1,1-dioxo-1,2-dihydro-1λ6-benzo[d]isothiazol-3-one and an organic base can be used to efficiently promote condensation of a nucleoside phosphoramidite and nucleoside monomer or a nascent oligonucleotide. Thus, one embodiment of the invention is a salt complex of the 1,1-dioxo-1,2-dihydro-1λ6-benzo[d]isothiazol-3-one represented by Structural Formula I and an organic base.

In the presence of an organic base, 1,1-dioxo-1,2-dihydro-1λ6-benzo[d]isothiazol-3-one has good solubility particularly in organic solvents that are typically used for oligonucleotide synthesis. Therefore, another embodiment of the invention is an activator solution that includes an organic solvent, an organic base and a 1,1-dioxo-1,2-dihydro-1λ6-benzo[d]isothiazol-3-one represented by Structural Formula I. The concentration of the 1,1-dioxo-1,2-dihydro-1λ6-benzo[d]isothiazol-3-one and the organic base in the activator solution can be up to the solubility of the 1,1-dioxo-1,2-dihydro-1,6-benzo[d]isothiazol-3-one in the solvent concerned. In a preferred embodiment, the 1,1-dioxo-1,2-dihydro-1λ6-benzo[d]isothiazol-3-one and the organic base are present in a concentration range of about 0.01 M to about 2M, for example from about 0.05M to about 0.5M. Commonly, the 1,1-dioxo-1,2-dihydro-1,6-benzo[d]isothiazol-3-one and the organic base are present at a concentration of up to 0.25M, such as from about 0.1M to about 0.25M. In a more preferred embodiment, the 1,1-dioxo-1,2-dihydro-1λ6-benzo[d]isothiazol-3-one and the organic base are present in the same molar concentration. In a preferred embodiment, the organic solvent comprises acetonitrile. In another preferred embodiment, the organic solvent comprises an organic amide, such as dimethylformamide, 1-methyl-2-pyrrolidinone or 1,3-dimethyl-2-imidazolidinone.

In another embodiment, an oligonucleotide can be synthesized using phosphoramidite chemistry in which the coupling agent is a 1,1-dioxo-1,2-dihydro-1,6-benzo[d]isothiazol-3-one represented by Structural Formula I. The coupling agent promotes condensation between a nucleoside or a nascent oligonucleotide having a free hydroxy or thiol group and a phosphoramidite. In a preferred embodiment, an organic base is present with the 1,1-dioxo-1,2-dihydro-1λ6-benzo[d]isothiazol-3-one during the coupling reaction. In a more preferred embodiment, the organic base is present in the same molar concentration as the 1,1-dioxo-1,2-dihydro-1λ6-benzo[d]isothiazol-3-one.

The nucleoside phosphoramidite can be a monomer or an oligomer, such as a dimer or a trimer. When the nucleoside phosphoramidite is a monomer it can be represented by represented by Structural Formula IIa:

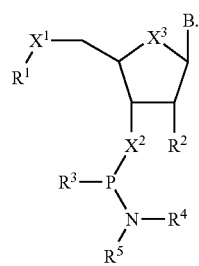

IIa

In Structural Formula IIa, X1 for each occurrence is, independently, —O— or —S—. Preferably, X1 is —O— at every occurrence. X2 for each occurrence is, independently, —O—, —S—, or —NR—. Preferably, X2 is —O— at every occurrence. X3 for each occurrence is, independently, —O—, —S—, —CH2-, or —(CH2)2-. Preferably, X3 is —O— at every occurrence. In a more preferred embodiment, X1, X2, and X3 are all —O— at every occurrence. R1 is an alcohol protecting group or a thio protecting group. Preferably, R1 is an acid labile protecting group. R2 for each occurrence is, independently, —H, —F —OR6, —NR7R8, —SR9, or a substituted or unsubstituted aliphatic group, such as methyl or allyl. R3 for each occurrence is, independently, —OCH2CH2CN, —SCH2CH2CN, a substituted or unsubstituted aliphatic group, —OR10, —SR10, —O—CH2CH2-Si(CH3)2C6H5, —O—CH2CH2-S(O)2-CH2CH3, —O—CH2CH2-C6H4-NO2, —S—CH2CH2-Si(CH3)2C6H5, —S—CH2CH2-S(O)2-CH2CH3, or —S—CH2CH2-C6H4-NO2. R4 and R5 are each, independently, a substituted or unsubstituted aliphatic group, a substituted or unsubstituted aryl group, a substituted or unsubstituted aralkyl. Alternatively, R4 and R5 taken together with the nitrogen to which they are bound form a heterocyclyl group. R6 for each occurrence is, independently, —H, a substituted or unsubstituted aliphatic group (e.g., methyl, ethyl, methoxyethyl or allyl), a substituted or unsubstituted aryl group, a substituted or unsubstituted aralkyl, an alcohol protecting group, or —(CH2)q-NR18R19. R7 and R8 for each occurrence are each, independently, —H, a substituted or unsubstituted aliphatic group, or an amine protecting group. Alternatively, R7 and R8 taken together with the nitrogen to which they are attached are a heterocyclyl group. R9 for each occurrence is, independently, —H, a substituted or unsubstituted aliphatic group, or a thio protecting group. R10 is for each occurrence is, independently, a substituted or unsubstituted aliphatic group, a substituted or unsubstituted aryl group or a substituted or unsubstituted aralkyl group. R18 and R19 are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group. Alternatively, R18 and R19 taken together with the nitrogen to which they are attached form a heterocyclyl group. q is an integer from 1 to about 6. B is —H, a natural or unnatural nucleobase, protected nucleobase, protected natural or unnatural nucleobase, heterocycle or a protected heterocycle.

In another embodiment, the phosphoramidite can be an oligomer, such as a dimer or trimer. Methods of preparing and utilizing nucleoside phosphoramidite dimers and trimers in phosphoramidite synthesis of oligonucleotides are disclosed in International Patent Application No. PCT/GB01/03973, the entire teachings of which are incorporated herein by reference.

The sugar moiety of the nucleoside phosphoramidite can have either a D configuration, as in naturally occurring DNA and RNA and as in Structural Formula Ia, or it can have an L configuration. Structural Formula IIb represents an L-nucleoside phosphoramidite:

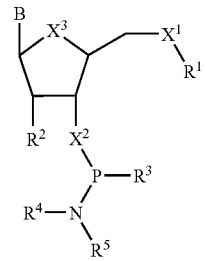

IIb

In Structural Formula IIb, X1, X2, X3, R1, R2, R3, R4, R5, and B are as defined above.

In another embodiment, the phosphoramidite group of the nucleoside phosphoramidite can be attached to the 5'-position of the sugar ring. In this embodiment, the nucleoside phosphoramidite can be represented by Structural Formulae IIIa and IIIb:

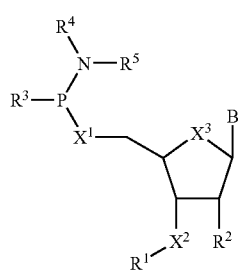

IIIa

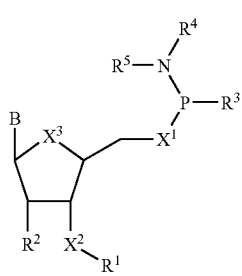

IIIb

In Structural Formulas IIIa and IIIb, X1, X2, X3, R1, R2, R3, R4, R5, and B are as defined above.

In another embodiment, the 1,1-dioxo-1,2-dihydro-1λ6-benzo[d]isothiazol-3-one can be used to promote condensation of a nascent n-mer oligonucleotide (i.e., an oligonucleotide having n nucleobases) and a nucleoside phosphoramidite to form an (n+1)-mer oligonucleotide. Preferably, the nucleoside phosphoramidite can be represented by Structural Formula Ia. The nascent oligonucleotide can be represented by Structural Formula IV:

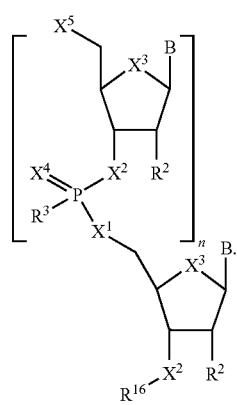

IV

In Structural Formula IV, X1, X2, X3, R2, R3, and B are as defined above. Each X4 for each occurrence is, independently, O or S. X5 for each occurrence is, independently, —OH or —SH. Preferably, X5 is —OH. R16 is a hydroxy protecting group, a thio protecting group, an amino protecting group, —(CH2)q-NR18R19, a solid support, or a cleavable linker attached to a solid support, such as a group of the formula —Y2-L-Y2-R15. Y2 for each occurrence is, independently, a single bond, —C(O)—, —C(O)NR17-, —C(O)O—, —NR17- or —O—. L is a linker which is preferably a substituted or unsubstituted aliphatic group or a substituted or unsubstituted aromatic group. More preferably, L is an ethylene group. R17 is —H, a substituted or unsubstituted aliphatic group or a substituted or unsubstituted aromatic group. R15 is any solid support suitable for solid phase oligonucleotide synthesis known to those skilled in the art. Examples of suitable solid supports include controlled-pore glass, polystyrene, microporous polyamide, such as poly(dimethylacrylamide), and polystyrene coated with polyethylene. In many embodiments, R16 represents a cleavable linker, such as a succinyl or oxaloyl linker, attached to a solid support. n is zero or a positive integer.

The nascent oligonucleotide is contacted with the phosphoramidite and a 1,1-dioxo-1,2-dihydro-1λ6-benzo[d]isothiazol-3-one represented by Structural Formula I.

In a preferred embodiment, an organic base is also present when the nascent oligonucleotide is contacted with the 1,1-dioxo-1,2-dihydro-1λ6-benzo[d]isothiazol-3-one. More preferably, the organic base is present in the same molar concentration as the 1,1-dioxo-1,2-dihydro-1λ6-benzo[d]isothiazol-3-one. The nascent oligonucleotide trivalent phosphorous linkage represented by Structural Formula V:

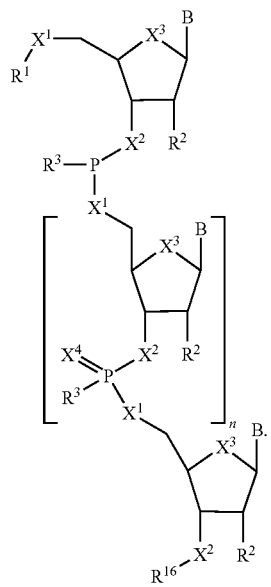

V

In Structural Formula V, X1, X2, X3, X4, R1, R2, R3, R16, B and n are defined as above.

The oligonucleotide represented by Structural Formula V can then be contacted with an oxidizing agent or a sulfurizing agent to form an oligonucleotide having a pentavalent phosphorous backbone represented by Structural Formula VI:

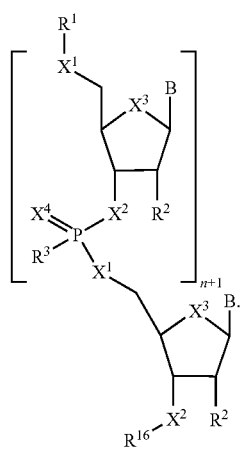

VI

In Structural Formula VI, X1, X2, X3, X4, R1, R2, R3, R16, B and n are defined as above.

After oxidizing or sulfurizing the (n+1) oligonucleotide, X5 groups which did not react with the phosphoramidite can be capped by conventional capping techniques known in the art. For example, the unreacted X5 groups can be reacted with an acid chloride or an anhydride in the presence of a base.

Typically, X5 groups are capped with acetyl chloride or acetic anhydride in pyridine.

After the oxidation or sulfurization step or after the capping step, the (n+1) oligonucleotide can be deprotected by reacting it with a reagent to remove R1. If R1 is an acid labile protecting group, the (n+1) oligonucleotide is treated with an acid to remove R1. If R1 is a trialkylsilyl group, such as t-butyldimethylsilyl group or a triisopropylsilyl group, the (n+1) oligonucleotide can be treated with fluoride ions to remove R1. Typically, t-butyldimethylsilyl and a triisopropylsilyl are removed by treatment with a solution of tetrabutylammonium fluoride in THF or with hydrogen fluoride and a conjugate base, such as $(C_2H_5)_3N \cdot 3HF$. Methods for removing t-butyldimethylsilyl can be found in Greene, et al., Protective Groups in Organic Synthesis (1991), John Wiley & Sons, Inc., pages 77-83, the teachings of which are incorporated herein by reference in their entirety. The above reaction steps, or reaction cycle, can be repeated one or more times to form an oligonucleotide of the desired length. When it is desired to obtain an oligonucleotide product in which the 5'-end group is protected, the final step of the reaction cycle can be the capping step, if a capping step is done, or the final step of the reaction can be an oxidation or sulfurization step if a capping step is not done. When the oxidation or sulfurization step or the capping step is the final step, the oligonucleotide can be represented by Structural Formula VII:

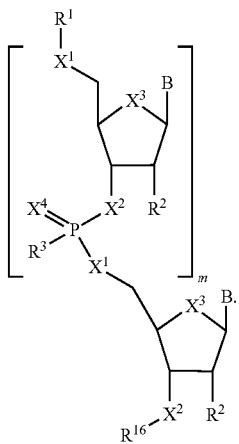

VII

In Structural Formula VII, X1, X2, X3, X4, R1, R2, R3, R16, and B are defined as above. m is an integer.

Alternatively, the final step of the reaction cycle can be removal of R1 if it is desired to obtain an oligonucleotide which does not have a 5'-protecting group. When removal of R1 is the final reaction step, the oligonucleotide can be represented by Structural Formula VIII:

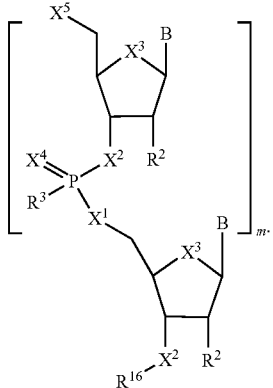

VIII

In Structural Formula VIII, X1, X2, X3, X4, X5, R1, R2, R3, R16, B and m are defined as above.

Oligonucleotides produced by the method of the present invention can be deprotected, and as appropriate cleaved from a solid support, using methods known in the art for the given protecting groups and/or solid support.

1,1-Dioxo-1,2-dihydro-1λ6-benzo[d]isothiazol-3-ones in the presence of an organic base promote phosphoramidite condensation reactions with at least equal efficiency as tetrazole. However, fewer undesirable side products are produced when a 1,1-dioxo-1,2-dihydro-1λ6-benzo[d]isothiazol-3-one is used instead of tetrazole. In addition, the complexes of the invention are non-explosive and therefore, safer to use than tetrazole particularly in large scale synthesis of oligonucleotides.

DETAILED DESCRIPTION OF THE INVENTION

Aliphatic groups, as used herein, include straight chained or branched C1-C18 hydrocarbons which are completely saturated or which contain one or more unconjugated double bonds, or cyclic C3-C18 hydrocarbons which are completely saturated or which contain one or more unconjugated double bonds. Alkyl groups are straight chained or branched C1-C8 hydrocarbons or C3-C8 cyclic hydrocarbons which are completely saturated. Aliphatic groups are preferably alkyl groups.

Aryl groups include carbocyclic aromatic ring systems (e.g., phenyl) and carbocyclic aromatic ring systems fused to one or more carbocyclic aromatic (e.g., naphthyl and anthracenyl) or an aromatic ring system fused to one or more non-aromatic ring (e.g., 1,2,3,4-tetrahydronaphthyl).

Heterocyclic groups, as used herein, include heteroaryl groups and heteroalicyclyl groups. Heteroaryl groups, as used herein, include aromatic ring systems that have one or more heteroatoms selected from sulfur, nitrogen or oxygen in the aromatic ring. Preferably, heteroaryl groups are five or six membered ring systems having from one to four heteroatoms. A heteroalicyclyl group, as used herein, is a non-aromatic ring system that preferably has five to six atoms and includes at least one heteroatom selected from nitrogen, oxygen, and sulfur. Examples of heterocyclic groups include morpholinyl, piperidinyl, piperazinyl, thiomorpholinyl, pyrrolidinyl, thiazolidinyl, tetrahydrothienyl, azetidinyl, tetrahydrofuryl, dioxanyl and dioxepanyl thienyl, pyridyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, oxadiazoles, benzo[b]thienyl, benzimidazole, indole, tetrahydroindole, azaindole, indazole, quinoline, imidazopyridine, purine, pyrrolo[2,3-d]pyrimidine, and pyrazolo[3,4-d]pyrimidine.

Azaheterocyclyl compounds, as used herein, include heteroaryl groups which have one or more nitrogen atom in the aromatic ring and heteroalicyclyl groups that have at least one nitrogen atom in the non-aromatic ring system. Preferably, azaheteroaryl compounds have five- or six-membered aromatic rings with from one to three nitrogens in the aromatic ring. Preferably, azaheteroalicyclyl compounds are five- or six-membered rings, commonly comprising one or two nitrogens in the ring. Preferred azaheterocyclyl compounds are organic bases. Examples of azaheterocyclyl compounds that are organic bases include pyrimidines, 1-alkylpyrazoles, especially 1-(C1-4 alkyl)pyrazoles, 1-arylpyrazoles, 1-benzylpyrazoles, pyrazines, N-alkylpurines, especially N—(C1-4 alkyl)purines, N-arylpurines, N-benzylpurines, N-alkylpyrroles, especially N—(C1-4 alkyl)pyrroles, N-arylpyrroles, N-benzylpyrroles, pyridines, N-alkylimidazoles, especially N—(C1-4 alkyl)imidazoles, N-arylimidazoles, especially N-phenylimidazole, N-benzylimidazoles, quinolines, isoquinolines, quinoxalines, quinazolines, N-alkylindoles, especially N—(C1-4 alkyl)indoles, N-arylindoles, N-benzylindoles, N-alkylbenzimidazoles especially N—(C1-4 alkyl)benzimidazoles, N-arylbenzimidazoles, N-benzylbenzimidazoles, triazine, thiazole, 1-alkyl-7-azaindoles, especially 1-(C1-4 alkyl-7-azaindoles, 1-aryl-7-azaindoles, 1-benzyl-7-azaindoles, pyrrolidines, morpholines, piperidines, and piperazines. Especially preferred azaheterocyclyl compounds are pyridines, such as pyridine and 3-methylpyridine, and N—(C1-4 alkyl) imidazoles, such as N-methylimidazole.

An aralkyl group, as used herein, is an aromatic substituent that is linked to a moiety by an alkyl group. Preferred aralkyl groups include benzyl groups.

A heteroaralkyl group, as used herein, is a heteroaryl substituent that is linked to a moiety by an alkyl group.

An organic base is an organic compound that has a tendency to accept protons at pH 7. Preferred organic bases are secondary amines, tertiary amines or azaheterocyclyl compounds, each of which may be substituted or unsubstituted by one or more substituents. An aprotic organic base is an organic base that has no hydrogen bonding protons in its chemical structure before accepting a proton. Aprotic organic bases such as tertiary amines and aprotic azaheterocyclyl compounds are preferably used in conjunction with 1,1-dioxo-1,2-dihydro-1λ6-benzo[d]isothiazol-3-ones, as described herein, to promote condensation reactions.

Tertiary amines are organic bases that have a nitrogen atom which is bonded to three carbon atoms, often to three aryl, commonly phenyl, and/or alkyl groups, commonly to three alkyl groups, including for example trialkylamines such as trimethylamine, triethylamine, and diisopropylethylamine. In addition, tertiary amines can be azaheterocyclyl groups wherein the nitrogen atom is aprotic. Tertiary amines that are azaheterocyclyl groups are preferred. Examples of azaheterocyclyl tertiary amines are N-alkylpyrrolidines, N-arylpyrrolidines, N-alkylpyrroles, N-arylpyrroles, N-alkylmorpholines, N-arylmorpholines, N-alkylpiperidines, N-arylpiperidines, N,N-dialkylpiperazines, N,N-diarylpiperazines, N-alkyl-N-aryl-piperazines, quinuclidines, and 1,8-diazabicyclo[5.4.0]undec-7-enes. Tertiary amines can also be azaheteroaryl or azaheteroalicyclyl compounds.

Secondary amines are organic bases comprising a nitrogen bonded to a single hydrogen and to two carbon atoms. Commonly the nitrogen atom is bonded to two alkyl or aryl groups or forms part of an azaheterocyclic group. Examples of secondary amine compounds include diethylamine and diisopropylamine.

Suitable substituents for aliphatic groups, aryl groups, aralkyl groups, heteroaryl groups, azaheteroaryl groups and heteroalicyclyl groups include aryl groups, halogenated aryl groups, alkyl groups, halogenated alkyl (e.g. trifluoromethyl and trichloromethyl), aliphatic ethers, aromatic ethers, benzyl, substituted benzyl, halogens, particularly chloro and fluoro groups, cyano, nitro, —S-(aliphatic or substituted aliphatic group), and —S-(aromatic or substituted aromatic).

Amine, hydroxy and thiol protecting groups are known to those skilled in the art. For examples of amine protecting groups see Greene, et al., Protective Groups in Organic Synthesis (1991), John Wiley & Sons, Inc., pages 309-405, the teachings of which are incorporated herein by reference in their entirety. Preferably, amines are protected as amides or carbamates. For examples of hydroxy protecting groups see Id., pages 10-142, the teachings of which are incorporated herein by reference in their entirety. A preferred hydroxy protecting group is t-butyldimethylsilyl group. For examples of thiol protecting groups see Id., pages 277-308, the teachings of which are incorporated herein by reference in their entirety.

An acid labile protecting group is a protecting group which can be removed by contacting the group with a Bronsted or a Lewis acid. Acid labile protecting groups are known to those skilled in the art. Examples of common acid labile protecting groups include substituted or unsubstituted trityl groups (Id., pages 60-62), substituted or unsubstituted tetrahydropyranyl groups (Id., pages 31-34), substituted or unsubstituted tetrahydrofuranyl groups (Id., pages 36-37) or pixyl groups (Id., page 65). Trityl groups are commonly substituted by electron donating substituents such as alkoxy groups. A preferred acid labile protecting group is a substituted or unsubstituted trityl, for example 4,4'-dimethoxytrityl (hereinafter "DMT").

Nucleoside bases include naturally occurring bases, such as adenine, guanine, cytosine, thymine, and uricil and modified bases such as 7-deazaguanine, 7-deaza-8-azaguanine, 5-propynylcytosine, 5-propynyluricil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouricil, 2,6-diaminopurine, 8-aminopurine, 4-triazolo-5-methylthymine, and 4-triazolo-5-methyluricil.

A protected nucleoside base is a nucleoside base in which reactive functional groups of the base are protected. Similarly, a protected heterocycle is a heterocycle in which reactive substitutents of the heterocycle are protected. Typically, nucleoside bases or heterocycles have amine groups which can be protected with an amine protecting group, such as an amide or a carbamate. For example, the amine groups of adenine and cytosine are typically protected with benzoyl protecting groups, and the amine groups of guanine is typically protected with an isobutyryl group, an acetyl group or t-butylphenoxyacetyl group. However, other protection schemes may be used. For example, for fast deprotection, the amine groups of adenine and guanine are protected with phenoxyacetyl groups and the amine group of cytosine is protected with an isobutyryl group or an acetyl group. Conditions for removal of the nucleobase or heterocycle protecting group will depend on the protecting group used. When an amide protecting group is used, it can be removed by treating the oligonucleotide with a base solution, such as a concentrated ammonium hydroxide solution, n-methylamine solution or a solution of t-butylamine in ammonium hydroxide.

The term "oligonucleotide," as used herein, includes naturally occurring oligonucleotides, for example 2'-deoxyribonucleic acids (hereinafter "DNA") and ribonucleic acids (hereinafter "RNA") and nucleic acids containing modified sugar moieties, modified phosphate moieties, or modified nucleobases. Modification to the sugar moiety includes replacing the ribose ring with a hexose, cyclopentyl or cyclohexyl ring. Alternatively, the D-ribose ring of a naturally occurring nucleic acid can be replaced with an L-ribose ring or the b-anomer of a naturally occurring nucleic acid can be replaced with the a-anomer. The oligonucleotide may also comprise one or more abasic moieties. Modified phosphate moieties include phosphorothioates, phosphorodithioates, methyl phosphonates, methyl phosphates, and phosphoramidates. Such nucleic acid analogs are known to those of skill in the art. Oligonuceotides comprising mixtures of two or more of the foregoing may be prepared, for example, oligonuceotides comprising mixtures of deoxyribo- and ribonucleosides, particularly mixtures of deoxyribonucleosides and 2'-O-substituted ribonucelosides, such as 2'-O-methyl or 2'-O-methoxyethyl ribonucleosides. Examples of oligonucleotides comprising mixtures of nucleosides include ribozymes.

A chimeric oligonucleotide is an oligonucleotide that has both phosphodiester and phosphorothioate linkages.

A synthetic oligonucleotide preferably has from 2 to about 100 nucleobases. More preferably, a synthetic oligonucleotide has 2 to about 75 nucleobases. Many synthetic oligonucleotides of current therapeutic interest comprise from 8 to 40 nucleobases.

The synthesis of the oligonucleotide can be done in solution or on a solid support. When the synthesis is in solution, R16 is an alcohol, amine or thiol protecting group. After synthesis of the oligonucleotide the alcohol, amine or thiol protecting group can be removed. When the oligonucleotide is synthesized on a solid support, R16 represents a solid support or preferably a cleavable linker attached to a solid support, such as a group of formula —Y2-L-Y2-R15. In general, the solution phase synthesis or the solid phase synthesis of oligonucleotides using a 1,1-dioxo-1,2-dihydro-1λ6-benzo[d]isothiazol-3-one compound instead of tetrazole to promote condensation of a nascent oligonucleotide and a phosphoramidite monomer is carried out similar to method which have been developed for synthesis of oligonucleotides using tetrazole as an activator. Examples of typical conditions for solution phase synthesis and solid phase synthesis oligonucleotides using a 1,1-dioxo-1,2-dihydro-1λ6-benzo[d]isothiazol-3-one compound to promote the condensation reaction are set forth below.

The first step of preparing the oligonucleotide involves coupling a nucleoside phosphoramidite, such as the phosphoramidite represented by Structural Formula IIa, with a nucleoside or nascent oligonucleotide that has a free hydroxy or thiol group, such as a 5-deprotected nucleoside or nascent oligonucleotide represented by Structural Formula IV. During the coupling reaction, the hydroxy or thiol group of the nucleoside or nascent oligonucleotide reacts with the nucleoside phosphoramidite by displacing the —NR4R5 group. When the synthesis is done in solution, the nucleoside or nascent oligonucleotide is often present in a concentration of about 0.001 M to about 1.0 M, and preferably the nucleoside or nascent oligonucleotide is present in a concentration of about 0.025 M to about 0.5 M. The nucleoside phosphoramidite is preferably present in a concentration of about 1.1 equivalents to about 2 equivalents with respect to the nucleoside or nascent oligonucleotide. From about 0.5 equivalents, often from about 2.5 equivalents, to about 5.0 equivalents, with respect to the nucleoside or nascent oligonucleotide, of a 1,1-dioxo-1,2-dihydro-1λ6-benzo[d]isothiazol-3-one is added to promote the condensation reaction. Preferably, the 1,1-dioxo-1,2-dihydro-1λ6-benzo[d]isothiazol-3-one is added as a salt complex with an organic base, such as a pyridinium salt, a 3-picolinium salt or an N-methylimidazolium salt. The reaction time is commonly about 20 min. to about 60 min., and an (n+1) nascent oligonucleotide with a terminal trivalent phosphorous linkage is formed, such as the nascent oligonucleotide represented by Structural Formula V.

A second step of preparing an oligonucleotide involves oxidizing or sulfurizing the terminal trivalent phosphorous group of the nascent oligonucleotide. In a solution phase synthesis, the oxidation reaction is often carried out by treating the oligonucleotide with an oxidizing agent such as I2 in the presence of water or a peroxide such as t-butyl hydrogen peroxide in an organic solvent. When I2 and water are used, the oxidizing solution typically contains about 1.1 to about 1.8 equivalents of I2 in the presence of a base and a trace amount of water. The reaction is carried out in an aprotic polar solvent, such as THF, combined with a base, such as a tertiary alkylamine and about 1% water. The ratio of aprotic solvent to base is about 4:1 (vol./vol.) to about 1:4 (vol./vol.). After about 5 min. to about 20 min., the reaction mixture is poured into an aqueous solution of sodium bisulfite to quench the excess iodine, then extracted into an organic solvent.

Alternatively, the terminal trivalent phosphorous group can be sulfurized using any sulfur transfer reagent known to those skilled in the art of oligonucleotide synthesis. Examples of sulfur transfer reagents include 3H-benzodithiol-3-one 1,1-dioxide (also called "Beaucage reagent"), dibenzoyl tetrasulfide, phenylacetyl disulfide, N,N,N',N'-tetraethylthiuram disulfide, elemental sulfur, and 3-amino-[1,2,4]dithiazole-5-thione (see U.S. Pat. No. 6,096,881, the entire teachings of which are incorporated herein by reference). Reaction conditions for sulfurization of an oligonucleotide using the above reagents can be found in Beaucage, et al., Tetrahedron (1993), 49:6123, the teachings of which are incorporated herein by reference in their entirety. 3-Amino-[1,2,4]dithiazole-5-thione is a preferred sulfur transfer reagent. Generally, an oligonucleotide is contacted with a solution of 3-amino-[1,2,4]dithiazole-5-thione in an organic solvent, such pyridine/acetonitrile (1:9) mixture or pyridine, having a concentration of about 0.05 M to about 0.2 M. The sulfurization reaction is commonly complete in about 30 sec. to about 2 min.

After oxidation or sulfurization of the oligonucleotide, any unreacted free hydroxy or thiol groups can be capped so that they cannot react in subsequent coupling steps. Capping failure sequences allows them to be more readily separated from full length oligonucleotide product. Any reagent which will react with a hydroxy or thiol group and prevent it from reacting with a phosphoramidite can be used as a capping reagent. Typically, an anhydride, such as acetic anhydride or isobutyric anhydride, or an acid chloride, such as acetyl chloride or isobutyryl chloride, in the presence of a base is used as a capping reagent.

After the capping reaction is complete, the R1 protecting group is removed. When R1 is an acid labile protecting group, R1 is removed by treating the oligonucleotide with an acid. Preferably, R1 is a trityl group, such as 4,4'-dimethoxytrityl. When the R1 is a trityl group, it can be removed by treating the oligonucleotide with a solution of dichloroacetic acid or trichloroacetic acid in an organic solvent, such as dichloromethane or toluene. Once the R1 protecting group has been removed, the reaction cycle (i.e., coupling step, oxidation or sulfurization step, capping step (optional) and deprotection step) optionally can be repeated one or more times to obtain an oligonucleotide of the desired length.

A chimeric oligonucleotide can be prepared by oxidizing the terminal trivalent phosphorous group in one or more reaction cycles and sulfurizing the terminal trivalent phosphorous group in one or more different reaction cycles. Alternatively, a chimeric oligonucleotide can be prepared by selecting phosphoramidite monomers in which some of the R3 groups are protected hydroxyl groups, such as —OCH2CH2CN, and some of the R3 groups are protected thiol groups, such as —SCH2CH2CN. In this method, the oligonucleotide is oxidized after the coupling step in each reaction cycle.

When it is desired to obtain an oligonucleotide product in which the R1 group remains, the final step of the reaction cycle can be the capping step, if a capping step is done, or the final step of the reaction can be an oxidation or sulfurization step if a capping step is not done. If an R1 deprotected oligonucleotide is desired, the reaction cycle can end with the deprotection step. Usually, an R1 protected oligonucleotide is the desired product if the oligonucleotide is to be purified by reverse phase high performance liquid chromatography (HPLC). If the oligonucleotide is to be purified by ion-exchange chromatography or electophoresis, an R1 deprotected oligonucleotide is usually the desired product.

The solid phase synthesis of an oligonucleotide using a 1,1-dioxo-1,2-dihydro-1λ6-benzo[d]isothiazol-3-one and, preferably, an organic base to promote condensation of a nucleoside phosphoramidite with a support bound nucleoside or nascent oligonucleotide having a free hydroxy group of thiol group generally utilizes the same reaction cycle and reagents as the solution phase synthesis. Commonly, the nucleoside is first loaded on the solid support to the maximum suitable for the particular resin used. For example, loading can be about 50 μmole to about 700 μmole per gram of support.

In the condensation step, a solution of nucleoside phosphoramidite, typically having a concentration of about 0.01 M to about 1 M, preferably about 0.1 M, in an organic solvent, such as acetonitrile, is reacted with the support bound nucleoside to form a nascent oligonucleotide having a terminal trivalent phosphorous linkage. If a nucleoside phosphoramidite represented by either Structural Formula Ia or IIb is used, the nascent oligonucleotide will have a 5'-terminal trivalent phosphorous linkage after completion of the coupling reaction. If a nucleoside phosphoramidite represented by either Structural Formula IIIa or IIIb is used, the nascent oligonucleotide will have a 3'-terminal trivalent phosphorous linkage after completion of the coupling reaction. Preferably, the nucleoside phosphoramidites used can be represented by Structural Formula Ia. A solution of the 1,1-dioxo-1,2-dihydro-1λ6-benzo[d]isothiazol-3-one having a concentration of about 0.015M to about 1.5 M, often from about 0.05M to about 0.5M, preferably from 0.1 to 0.25M, is usually mixed with the solution containing the phosphoramidite monomer just prior to or during the condensation reaction. Preferably, an organic base is also present in the solution at a concentration of about 0.015M to about 1.5 M, often from about 0.05M to about 0.5M, preferably from 0.1 to 0.25M. Preferably, the organic base is present in the same molar concentration as the 1,1-dioxo-1,2-dihydro-1λ6-benzo[d]isothiazol-3-one. The 1,1-dioxo-1,2-dihydro-1λ6-benzo[d]isothiazol-3-one may be employed at a mole ratio to nucleoside phosphoramidite which is catalytic, that is sub-stoichiometric, or at a mole ratio which is stoichiometric or greater than stoichiometric. In many embodiments, the mole ratio of 1,1-dioxo-1,2-dihydro-1λ6-benzo[d]isothiazol-3-one to nucleoside phosphoramidite is in the range of from about 0.2:1 to 5:1, often from 0.25:1 to 4:1, preferably from about 0.3:1 to 2:1, for example about 1:1. Then the support bound 5'-deprotected nucleoside is contacted with the mixture for about 2 min. to about 10 min., preferably about 5 min.

If the terminal trivalent phosphorous linkage is to be oxidized after the coupling reaction is complete, the solid support containing the nascent oligonucleotide is contacted with an oxidizing agent such as a mixture of I2 and water or a peroxide such as t-butyl hydroperoxide in an organic solvent such as acetonitrile or toluene. A mixture of I2 and H2O is a preferred oxidizing reagent. When a mixture of I2 and water is used other water miscible organic solvents can also be present. Typically, the solid support bound oligonucleotide containing trivalent phosphorous internucleotide linkages can be contacted with a solution of I2 in a solvent mixture of water, an aprotic, water miscible solvent, and a base. An example of a typical oxidation solution is about 0.05 M to about 1.5 M I2 in a solution of (2:80:20) water/tetrahydrofuran/lutidine (vol./vol./vol.). The solid support is typically treated with the I2 solution for about 30 seconds to about 1.5 min.

Alternatively, the solid support bound nascent oligonucleotide can be contacted with a solution of a sulfur transfer reagent in an organic solvent to sulfurize the trivalent phosphorous groups. For example, the support bound oligonucleotide can be contacted with a solution of 3-amino-[1,2,4]-dithiazole-5-thione (about 0.05 M-0.2 M) in an organic solvent, such as acetonitrile or pyridine, for about 30 sec. to about 2 min.

In solid phase oligonucleotide synthesis, the solid support bound nascent oligonucleotide optionally can be contacted with a solution of the capping reagent for about 30 sec. to about 1 min. Following the capping step, the deprotection step is accomplished by contacting the support bound oligonucleotide with an acid solution for about 1 min. to about 3 min. The reaction cycle can optionally be repeated one or more times until an oligonucleotide of the desired length is synthesized. As in the solution phase synthesis, an R1 protected oligonucleotide is obtained when the reaction cycle ends with either the capping step or the oxidation or sulfurization step. An R1 deprotected oligonucleotide is obtained when the reaction cycle is ended with the deprotection step.

When the solid phase synthesis is completed, the oligonucleotide can be removed from the solid support by standard methods. Generally, the solid support is treated with a solution of concentrated ammonium hydroxide at 25° C.-60° C. for about 0.5 hours to about 16 hours or longer depending on the oligonucleotide sequence and whether it is desired to remove the nucleobase protecting groups during this step. The oligonucleotides are advantageously purified by methods known in the art, such as one or more of ion-exchange chromatography, reverse phase chromatography, and precipitation from an appropriate solvent. Further processing of the product by for example ultrafiltration may also be employed.

A particularly preferred aspect of the present invention comprises a method for the synthesis of an oligonucleotide comprising coupling a nucleoside phosphoramidite, preferably a nucleoside 3'-phosphoramidite, with a nucleoside or nascent oligonucleotide comprising a free hydroxy group, preferably a free 5'-hydroxy group, in the presence of an activator, wherein the activator comprises a mixture of a 1,1-dioxo-1,2-dihydro-1λ6-benzo[d]isothiazol-3-one and an N-alkylimidazole, preferably N-methylimidazole.

In this particularly preferred embodiment, the phosphoramidite commonly comprises a moiety of formula —P(OCH2CH2CN)N(CH(CH3)2)2. Commonly, in this embodiment, the concentration of each of the 1,1-dioxo-1,2-dihydro-1λ6-benzo[d]isothiazol-3-one and N-alkylimidazole is from 0.1 to 0.25M, and preferably the mole ratio of 1,1-dioxo-1,2-dihydro-1λ6-benzo[d]isothiazol-3-one to N-alkylimidazole is about 1:1 to about 1:1.5:1, most preferably 1:1. In this particularly preferred embodiment, the mole ratio of 1,1-dioxo-1,2-dihydro-1λ6-benzo[d]isothiazol-3-one to phosphoramidite is preferably from 0.5:1 to 2:1.

The present invention is illustrated without limitation by the following Examples.

EXAMPLE 1

Preparation a Salt Complex of 1,1-Dioxo-1,2-dihydro-1λ6-benzo[d]isothiazol-3-one and Pyridine 1,1-Dioxo-1,2-dihydro-1λ6-benzo[d]isothiazol-3-one was suspended in acetonitrile, and 1.1 eq. of pyridine with respect to the 1,1-dioxo-1,2-dihydro-1λ6-benzo[d]isothiazol-3-one was added dropwise to the suspension. The solution turned clear at the end of the addition, and a salt complex of 1,1-dioxo-1,2-dihydro-1λ6-benzo[d]isothiazol-3-one and pyridine separated out of the solution as a fine crystalline material. The crystals were washed with either ether or hexane to remove traces of pyridine and acetonitrile. 1H NMR (DMSO) chemical shifts in ppm: 8.8 (2H, s), 8.2 (1H, q), 8.0 (1H, q) and 7.6-7.9 (6H, m).

EXAMPLE 2

Preparation a Salt Complex of 1,1-Dioxo-1,2-dihydro-1λ6-benzo[d]isothiazol-3-one and 3-Picoline A salt complex of 1,1-dioxo-1,2-dihydro-1λ6-benzo[d]isothiazol-3-one and 3-picoline was prepare in the same manner as described in Example 1. 1H NMR (DMSO) chemical shifts in ppm: 8.8 (1H, s), 8.72 (1H, d), 8.27 (1H, d), 8.0 (2H, d), 7.77-7.93 (6H, m) and 2.45 (3H, s).

EXAMPLE 3

Preparation a Salt Complex of 1,1-Dioxo-1,2-dihydro-1λ6-benzo[d]isothiazol-3-one and N-Methylimidazole 1,1-Dioxo-1,2-dihydro-1λ6-benzo[d]isothiazol-3-one was suspended in acetonitrile, and 1.1 eq. of N-methylimidazole with respect to the 1,1-dioxo-1,2-dihydro-1λ6-benzo[d]isothiazol-3-one was added dropwise to the suspension. The reaction mixture was concentrated under reduced pressure to form the crystalline salt which was washed with either ether or hexane to remove traces of N-methylimidazole and acetonitrile. 1H NMR (DMSO) chemical shifts in ppm: 13.9 (1H, s), 9.03 (1H, s), 7.59-7.75 (6H, m) and 3.88 (3H, s),

EXAMPLE 4

Synthesis of deoxyribo-oligonucleotides using a salt complex of 1,1-dioxo-1,2-dihydro-1λ6-benzo[d]isothiazol-3-one and an organic Base Synthesis of the oligonucleotide was carried out on DNA synthesizer Oligo Pilot II (Amersham Pharmacia Biotech). The standard phosphoramidite chemistry protocol was followed for the synthesis with slight modifications. The concentration of phosphoramidite monomers was 0.1 M in acetonitrile. The salt complex of 1,1-dioxo-1,2-dihydro-1λ6-benzo[d]isothiazol-3-one and pyridine, 3-picoline or N-methylimidazole was used in place of tetrazole as the activator during the condensation step. The concentration of the salt complex was 0.25 M in acetonitrile. The coupling time used for the chain elongation using the 1,1-dioxo-1,2-dihydro-1λ6-benzo[d]isothiazol-3-one salt complex were similar to coupling times used when tetrazole is activator. After the condensation step, the phosphite triester linkage was converted either to stable phosphate triester with iodine solution or to stable phosphorothioate triester with Beaucage reagent or 3-amino-1,2,4,-dithiazole-5-thione. At the end of the synthesis, solid supports linked with fully protected oligonucleotide were treated with 10% t-butylamine in concentrated ammonium hydroxide for 16-20 hr at 50° C. in order to release the oligonucleotide and to remove the β-cyanoethyl protecting groups and the nucleobase protecting groups. The crude oligonucleotides were analyzed by ion exchange HPLC, capillary electrophoresis and MALDI-TOF mass spectrometry and were compared to oligonucleotides prepared using tetrazole as the activator. Table 1 describes the conditions used to synthesize phosphorothioate oligonucleotide sequence 5' TCT-CCC-AGC-GTG-CGC-CAT 3' (SEQ ID NO 1), and Table 2 describes the results obtained from the various syntheses. The salt complex illustrated in Tables 1 and 2 is 1,1-dioxo-1,2-dihydro-1λ6-benzo[d]isothiazol-3-one and N-methylimidazole.

TABLE 1

Synthesis Parameters for synthesis of SEQ ID NO 1.

| Solid Support | Scale of synthesis | Activator | Molar equiv. of Amidite | Activator vs. Amidite | Equiv. of sulfurizing agent |
|---|---|---|---|---|---|
| CPG-beads | 746 μmole | Tetrazole | 2.0 equ. | 4.3 | 3.2 |
| CPG-beads | 737 μmole | salt-complex | 2.0 equ. | 4.0 | 3.3 |
| CPG-beads | 737 μmole | salt-complex | 1.5 equ. | 3.3 | 3.3 |
| Rigid PS | 626 μmole | salt-complex | 2.0 equ. | 4.0 | 3.8 |
| Rigid PS | 600 μmole | Tetrazole | 2.0 equ. | 4.3 | 4.0 |

TABLE 2

Analysis and results of SEQ ID NO 1.

| Solid supports | Scale | Activator | mol equ. of amidite | Total OD units | FLP by CGE | FLP by HPLC | Mol. Wt. |
|---|---|---|---|---|---|---|---|
| CPG beads | 746 μmol | Tetrazole | 2.0 equ. | 84504 | 74% | 77% | 5688 |
| CPG beads | 737 μmol | Com Salt | 2.0 equ. | 82134 | 77% | 79% | 5687 |
| CPG beads | 737 μmol | Com. Salt | 1.5 equ. | 82320 | 77% | 79% | 5689 |
| Rigid PS | 626 μmol | Com. Salt | 2.0 equ. | 80712 | 76% | 76% | 5686 |
| Rigid PS | 600 μmol | Tetrazole | 2.0 equ. | 75006 | 73% | 71% | 5687 |

FLP = full length product, CGE = capillary gel electrophoresis, HPLC = Ion exchange HPLC While this invention has been particularly shown and described with references to preferred embodiments thereof, it will be understood by those skilled in the art that various changes in form and details may be made therein without departing from the scope of the invention encompassed by the appended claims.

What is claimed is:

1. A composition of matter for use in condensation reactions in the preparation of oligonucleotides comprising acetonitrile and an activator comprising an N-alkylimidazole and a 1,1-dioxo-1,2-dihydro-1$\lambda^6$-benzo[d]isothiazol-3-one represented by the following structural formula:

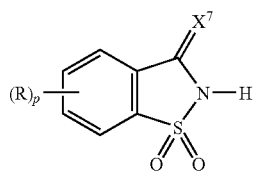

wherein:

p is 0 or an integer from 1 to 4;

$X^7$ is O or S; and

R for each occurrence is a substituent selected from the group consisting of halo groups, aliphatic groups, —$NR^{11}R^{12}$, —$OR^{13}$, —$OC(O)R^{13}$, —$C(O)OR^{13}$, cyano, aryl groups, heterocyclyl groups, —CHO, —$COR^{13}$, —$NHCOR^{13}$, aralkyl groups, and —$SR^{13}$; or two adjacent R groups taken together with the carbon atoms to which they are attached form a six membered saturated or unsaturated ring; wherein:

$R^{11}$ and $R^{12}$ are each, independently, —H, an aliphatic group, an aryl group, an aralkyl group; or together with the nitrogen to which they are attached form a 5 or 6-membered heterocyclic ring ; and $R^{13}$ is an aliphatic group, an aryl group, or an aralkyl group.

2. A composition of matter according to claim 1, wherein p is 0, $X^7$ is O and the concentration of the N-alkylimidazole and 1,1-dioxo-1,2-dihydro-1$\lambda^6$-benzo[d]isothiazol-3-one is from 0.1M to 0.25M.

3. A composition of matter for use in condensation reactions in the preparation of oligonucleotides comprising acetonitrile, N-methylimidazole and a compound of formula:

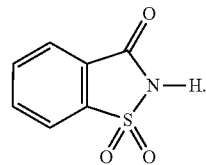

* * * * *